US012453538B2

(12) United States Patent
Mangan et al.

(10) Patent No.: US 12,453,538 B2
(45) Date of Patent: Oct. 28, 2025

(54) NASOPHARYNGEAL ASPIRATE COLLECTION DEVICE

(71) Applicant: Core Diagnostics Corporation, Georgetown, TX (US)

(72) Inventors: Wilma Mangan, Santa Clara, CA (US); John Haughey, Georgetown, TX (US)

(73) Assignee: Core Diagnostics Corporation, Georgetown, TX (US)

( * ) Notice: Subject to any disclaimer, the term of this patent is extended or adjusted under 35 U.S.C. 154(b) by 359 days.

(21) Appl. No.: 17/368,680

(22) Filed: Jul. 6, 2021

(65) Prior Publication Data

US 2022/0008045 A1 Jan. 13, 2022

Related U.S. Application Data

(60) Provisional application No. 63/049,662, filed on Jul. 9, 2020.

(51) Int. Cl.
*A61B 10/00* (2006.01)

(52) U.S. Cl.
CPC ................................ *A61B 10/0051* (2013.01)

(58) Field of Classification Search
CPC ....... A61B 10/0051; A61M 1/67; A61M 1/68; A61M 1/682; A61M 1/684; B01L 3/502
See application file for complete search history.

(56) References Cited

U.S. PATENT DOCUMENTS

| | | | | |
|---|---|---|---|---|
| 5,643,202 A * | 7/1997 | Gravenstein | A61B 10/02 | 604/514 |
| 8,827,945 B2 * | 9/2014 | Baker | A61M 1/72 | 604/35 |
| 2008/0154183 A1 * | 6/2008 | Baker | A61M 1/772 | 604/28 |
| 2009/0281485 A1 * | 11/2009 | Baker | A61M 1/70 | 604/35 |
| 2011/0224642 A1 * | 9/2011 | Fojtik | A61M 1/67 | 604/207 |

OTHER PUBLICATIONS

Biom'Up SA, PMA P170012: FDA Summary of Safety and Effectiveness Data, Dec. 15, 2017, HEMOBLAST™ Bellows, FDA, https://www.accessdata.fda.gov/cdrh_docs/pdf17/P170012B.pdf, pp. 1-3 (Year: 2017).*

* cited by examiner

*Primary Examiner* — Jason M Sims
*Assistant Examiner* — Matthew Eric Ogles
(74) *Attorney, Agent, or Firm* — McGuire Woods LLP

(57) ABSTRACT

Methods and systems directed towards a single use nasopharyngeal aspirate collection device comprise a reservoir capable of contracting and expanding in a lineal motion at least one time, a nozzle comprising an at least one orifice at a distal end of the nozzle, a fastener capable of coupling a proximal end of the reservoir with a proximal end of the nozzle, a guard disposed about a portion of an outer wall of the reservoir adjacent to the proximal end of the reservoir, and an internal cavity extending from the reservoir through the nozzle.

17 Claims, 6 Drawing Sheets

NASOPHARYNGEAL ASPIRATE COLLECTION DEVICE

BACKGROUND

The collection of fluid or tissue samples is often required in the diagnosis and treatment of subjects suffering from a number of diseases and medical conditions. Sample collection from the mouth, nose, throat and other locations can be accomplished by brushing or scraping the body surface with a swab. For example, some diseases may be detected by analyzing a swab, such as a throat swab, a nose swab, a check swab, or other swabs, or fluid obtained from a swab, such as: influenza and other respiratory disorders; tuberculosis; bacterial infections such as diphtheria, pertussis and bacterial infections caused by staphylococci, streptococci, pneumococci and other bacteria; viral infections, such as, for example, adenovirus infections; some genetic diseases caused by or associated with a genetic trait of a subject; and other diseases and conditions. Diseases can also be detected by analyzing urine samples and other clinical samples. After the sample has been collected, the sample may then be tested and analyzed at home or in-clinic using a testing apparatus or the collected sample may be sent to an off-site location for testing and analysis.

Nasal swabs require a much larger volume of a live virus to be present in the sample for an accurate test to be performed on the sample when compared with nasopharyngeal aspirates. Current methods for obtaining nasopharyngeal aspirates require relatively large amounts of a live virus to be present in a nasal swab specimen to perform a valid test. A sample obtained by aspiration may result in more accurate results. Nasopharyngeal aspirates or nasal wash specimens are generally considered the specimens of choice for the detection of respiratory viruses. Unfortunately, obtaining an aspirate using conventional nasal aspirators can be cumbersome, and it may require a suction device such as an electric suction device.

SUMMARY

Provided are apparatus for a nasopharyngeal aspirate collection device in accordance with the disclosure and the illustrated FIGURES. An example apparatus comprises a reservoir capable of contracting and expanding in a lineal motion at least one time; a nozzle comprising an at least one orifice at a distal end of the nozzle; a fastening means capable of coupling a proximal end of the reservoir with a proximal end of the nozzle; a guard disposed about a portion of an outer wall of the reservoir adjacent to the proximal end of the reservoir; and an internal cavity extending from the reservoir through the nozzle.

Additionally or alternatively, the apparatus may include one or more of the following features individually or in combination. The nasopharyngeal aspirate collection device may be a single use device. The nasopharyngeal aspirate collection device may further comprise a cap. The distal end of the nozzle may comprise three orifices; wherein two orifices are crescent-shaped and border the third orifice which is disposed between the two crescent-shaped orifices. The distal end of the nozzle may comprise a half-domed shape which extends inward toward the proximal end of the nozzle. The nasopharyngeal aspirate collection device may further comprise a cap with a half-domed shape which corresponds to the half-domed shape of the nozzle when the cap is placed over the nozzle. The reservoir may be a single reservoir which contains aspiration fluid before use and a collected sample after use. At least a portion of the nasopharyngeal aspirate collection device may comprise a polymer. The nozzle may be connected to the reservoir with a threaded connection. The nozzle may be connected to a cap with a threaded connection. If the nozzle comprises at least two orifices, the nasopharyngeal aspirate collection device may further comprises a diaphragm which restricts fluid flow outward from the nasopharyngeal aspirate collection device through at least one orifice. The diaphragm may comprise a flexible material which allows fluid flow into the reservoir through the orifice which was restricted in the outward direction. The diaphragm may comprise silicon.

Provided are methods for collecting a sample with a nasopharyngeal aspirate collection device in accordance with the disclosure and the illustrated FIGURES. An example method comprises inserting the nasopharyngeal aspirate collection device into a cavity of a subject, ejecting an aspiration fluid into the cavity from the nasopharyngeal aspirate collection device by applying pressure to a reservoir containing the aspiration fluid, removing pressure from the reservoir to create negative pressure in the reservoir, and withdrawing at least a portion of the aspiration fluid and a subject sample from the cavity into the reservoir.

Additionally or alternatively, the method may include one or more of the following features individually or in combination. The nasopharyngeal aspirate collection device may comprise a nozzle comprising an at least one orifice at a distal end of the nozzle; a fastening means capable of coupling a proximal end of the reservoir with a proximal end of the nozzle; a guard disposed about a portion of an outer wall of the reservoir adjacent to the proximal end of the reservoir; and an internal cavity extending from the reservoir through the nozzle. The method may further comprise removing the sample from the reservoir by detaching the reservoir; wherein the nasopharyngeal aspirate collection device is disposed of after the sample is removed. The nasopharyngeal aspirate collection device may further comprise a cap. The nasopharyngeal aspirate collection device may comprise a nozzle having a distal end, and wherein the distal end of the nozzle comprises three orifices; wherein two orifices are crescent-shaped and border the third orifice which is disposed between the two crescent-shaped orifices. The distal end of the nozzle may comprise a half-domed shape which extends inward toward the proximal end of the nozzle. The nasopharyngeal aspirate collection device may further comprise a cap with a half-domed shape which corresponds to the half-domed shape of the nozzle when the cap is placed over the nozzle. The reservoir may be a single reservoir which contains aspiration fluid before use and a collected sample after use. The aspiration fluid may be a saline solution. The cavity may be a nasal cavity. If the nozzle comprises at least two orifices, the nasopharyngeal aspirate collection device may further comprises a diaphragm which restricts fluid flow outward from the nasopharyngeal aspirate collection device through at least one orifice. The diaphragm may comprise a flexible material which allows fluid flow into the reservoir through the orifice which was restricted in the outward direction. The diaphragm may comprise silicon.

DETAILED DESCRIPTION

The nasopharyngeal aspirate collection device may be any device capable of sequentially delivering an aspiration fluid to the nasal cavity and then aspirating the nasopharyngeal fluid sample from the nasal cavity in a single step and should not be limited herein. Any suitable aspiration fluid may be pre-loaded into a reservoir of the nasopharyngeal aspirate collection device and should not be limited herein. Suitable aspiration fluids may include, but are not limited to, a saline solution, a sterile solution, the like, and/or any combinations thereof. Any aspiration fluid capable of washing the walls of the nasal cavity, the nasopharynx, the adenoid pad, and the like, thereby providing a mucosal sample for aspiration may be used and should not be limited herein.

The nasopharyngeal aspirate collection device may be formed in any suitable manner including, but not limited to, injection molding, extrusion, blow extrusion, fill extrusion, the like, and/or any combinations thereof. In a non-limiting example, the nasopharyngeal aspirate collection device may comprise any suitable material. Suitable materials may include any FDA approved plastic for class II and class III medical devices. In a non-limiting example, suitable materials may include, polymers, resins, elastomers, polyethylene, polypropylene, silicone, nylon, acetal, polyvinyl chloride, polyvinylidene fluoride, the like, and/or any combinations thereof. In a non-limiting example, each component of the nasopharyngeal aspirate collection device may be formed of the same material, different materials, and/or any combinations thereof.

Figure 1A:
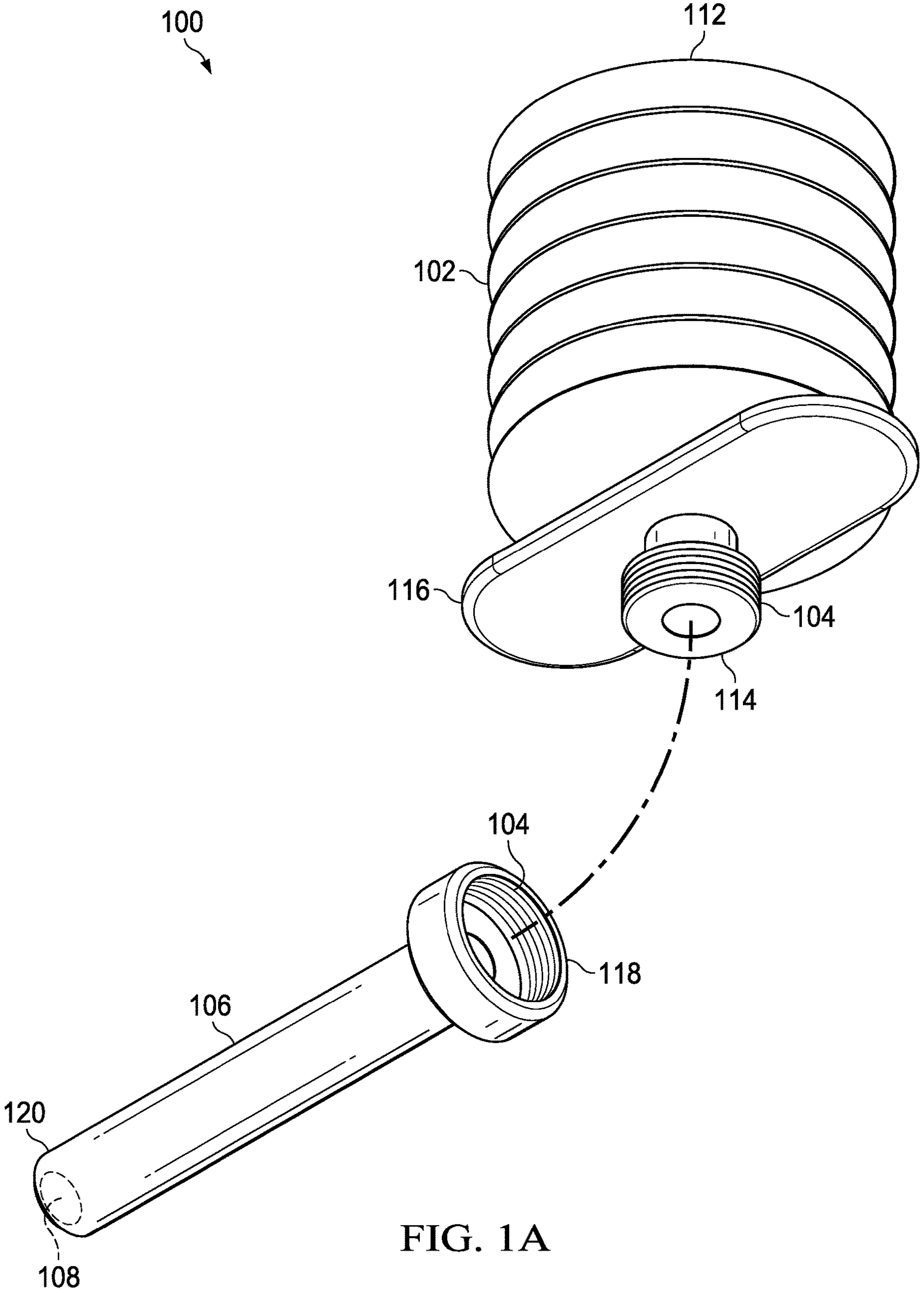
FIG. 1A illustrates an embodiment of an expanded view of a nasopharyngeal aspirate collection device.
Figure 1B:
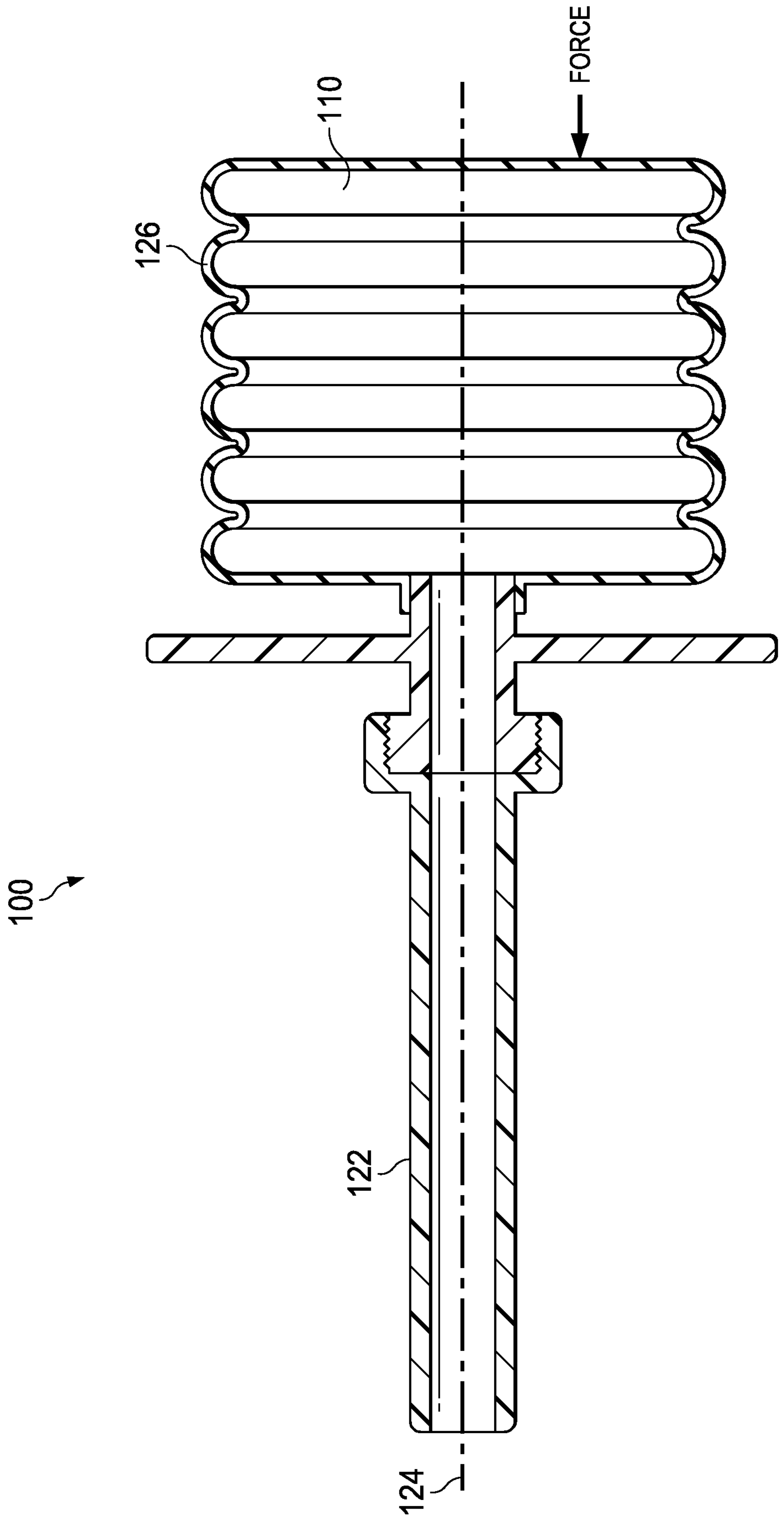
FIG. 1B illustrates an embodiment of a cross-sectional view of a nasopharyngeal aspirate collection device.

FIGS. 1A and 1B illustrate an embodiment of a nasopharyngeal aspirate collection device 100. The nasopharyngeal aspirate collection device 100 may comprise a reservoir 102, a fastening means 104, a nozzle 106 comprising at least one orifice 108, and an internal cavity 110. In a non-limiting example, the internal cavity 110 may extend from an enclosed distal end of the reservoir 112 and through the nozzle 106 thereby connecting the reservoir 102 with the at least one orifice 108.

The reservoir 102 may be any suitable reservoir 102 capable of contracting and expanding in a lineal motion at least one time. In an embodiment, the reservoir 102 may comprise an outer wall, an internal cavity 110, an enclosed distal end 112, an at least partially open proximal end 114 opposite the enclosed distal end 112, the like, and/or any combinations thereof. The reservoir 102 may be of any suitable size and shape capable of housing and/or storing an aspiration fluid, a collected aspiration fluid comprising a biological sample, a nasopharyngeal fluid sample, a saline solution, a sterile solution, the like, and/or any combinations thereof. The reservoir 102 may be of any suitable size and should not be limited herein.

The reservoir 102 may be of any suitable shape for a given application and should not be limited herein. Suitable shapes may include, but are not limited to, a cylinder, a sphere, a cube, a bellow, a triangular pyramid, a square pyramid, a triangular prism, a rectangular prism, trapezoidal prism, hexagonal prism, a pentagonal prism, the like, and/or any combinations thereof. In certain embodiments, the outer wall 126 of the reservoir 102 may be sloped at any suitable angle relative to the center axis 124 of the reservoir 102 and should not be limited herein. Optionally, the outer wall 126 of the reservoir 102 may not be sloped at an angle relative to the center axis 124 of the reservoir 102. The outer wall 126 of the reservoir 102 may be of any suitable profile for a given application and should not be limited herein.

Optionally, the reservoir 102 may further comprise a guard 116 disposed about a portion of the outer wall 126 of the reservoir 102 adjacent to the proximal end 114 of the reservoir 102. In a non-limiting example, guard 116 may be used by the user to help grip and hold the nasopharyngeal aspirate collection device 100 during use. In another non-limiting example, guard 116 may be used to prevent the nozzle 106 from penetrating the nasal cavity in a harmful manner such as, going too deep into the nasal cavity thereby causing irritation and/or injury to the patient. Optionally, the nozzle 106 may penetrate the nasal cavity at a depth of no more than about 1.25 inches from the entrance of the nasal cavity accessible by the user. The guard 116 may be of any suitable size and shape and should not be limited herein.

The nasopharyngeal aspirate collection device 100 may further comprise a fastening means 104 capable of coupling a proximal end 118 of a nozzle 106 with the proximal end 114 of the reservoir 102. Any suitable fastening means 104 may be used and should not be limited herein. Suitable fastening means 104 may include, but are not limited to, adhesives, fasteners, mating parts, the like, and/or any combinations thereof. Optionally, the proximal end 118 of the nozzle 106 may be permanently or semi-permanently coupled to the proximal end 114 of the reservoir 102.

The nasopharyngeal aspirate collection device 100 may further comprise a nozzle 106. The nozzle 106 may be of any suitable size and shape capable of penetrating the nasal cavity up to about 1.25 inches from the entrance of the nasal cavity accessible by the user. Suitable shapes may include, but are not limited to, cylinders, spheres, cones, the like, and/or any combinations thereof. The nozzle 106 may further comprise an outer surface 122, an internal cavity 110, at least one orifice 108 located at the distal end 120 of the nozzle 106, and a proximal end 118 of the nozzle 106, the like, and any combinations thereof. In an embodiment, the outer surface 122 of nozzle 106 may be substantially smooth. Optionally, the outer surface 122 of nozzle 106 may be sloped at any suitable angle relative to the center axis 124 of the nozzle 106 and should not be limited herein. Optionally, the outer surface 122 of nozzle 106 may not be sloped at an angle relative to the center axis 124 of the nozzle 106. The outer surface 122 of nozzle 106 may be of any suitable profile for a given application and should not be limited herein.

The nozzle 106 may further comprise an at least one orifice 108 located at the distal end 120 of the nozzle 106 capable of emitting aspiration fluid into the nasal cavity and withdrawing nasopharyngeal fluid sample from the nasal cavity. The orifice may be of any suitable size and shape and should not be limited herein. Suitable shapes may include, but are not limited to, a circle, an oval, a square, a rectangle, a triangle, the like, and/or any combinations thereof. In a non-limiting example, nozzle 106 may comprise a plurality of orifices. In a non-limiting example, orifice 108 and/or a plurality of orifices 108 may be disposed along the outer surface 122 of the nozzle 106, at the tip of nozzle 106, the like, and/or any combinations thereof. A diaphragm 138, illustrated in FIG. 3 below, may be placed within or proximate the interior of the nozzle 106 to control the orifices from which the aspiration fluid may be ejected from. For example, if the distal end 120 of the nozzle 106 comprises three orifices 108, the diaphragm 138 may limit the aspiration fluid to be ejected from only one of the orifices 108. Thus, the other orifices 108 may be limited in function to serving solely as returns for the collected sample. The diaphragm 138 may be made of a flexible material which flexes to allow the aspirated fluid to be returned to the reservoir 102 once applied pressure on the reservoir 102 is released and a negative pressure created in the reservoir 102.

Optionally, the nozzle 106 may further comprise a tip disposed at the proximal end 118 of the nozzle 106. The tip may be any tip capable of spraying and/or injecting an aspiration fluid into a nasal cavity and after a time has passed, aspirating the nasopharyngeal fluid sample from the nasal cavity. The tip may be formed in any suitable manner and should not be limited herein. Optionally, nozzle 106 may further comprise a means for releasing excess air from the nasopharyngeal aspirate collection device 100 before the device is used to spray and/or inject an aspiration fluid into the nasal cavity. Any suitable means capable of releasing excess air may be used and should not be limited herein. Suitable means may include, but are not limited to, valves, flaps, the like, and/or any combinations thereof.

Figure 2:
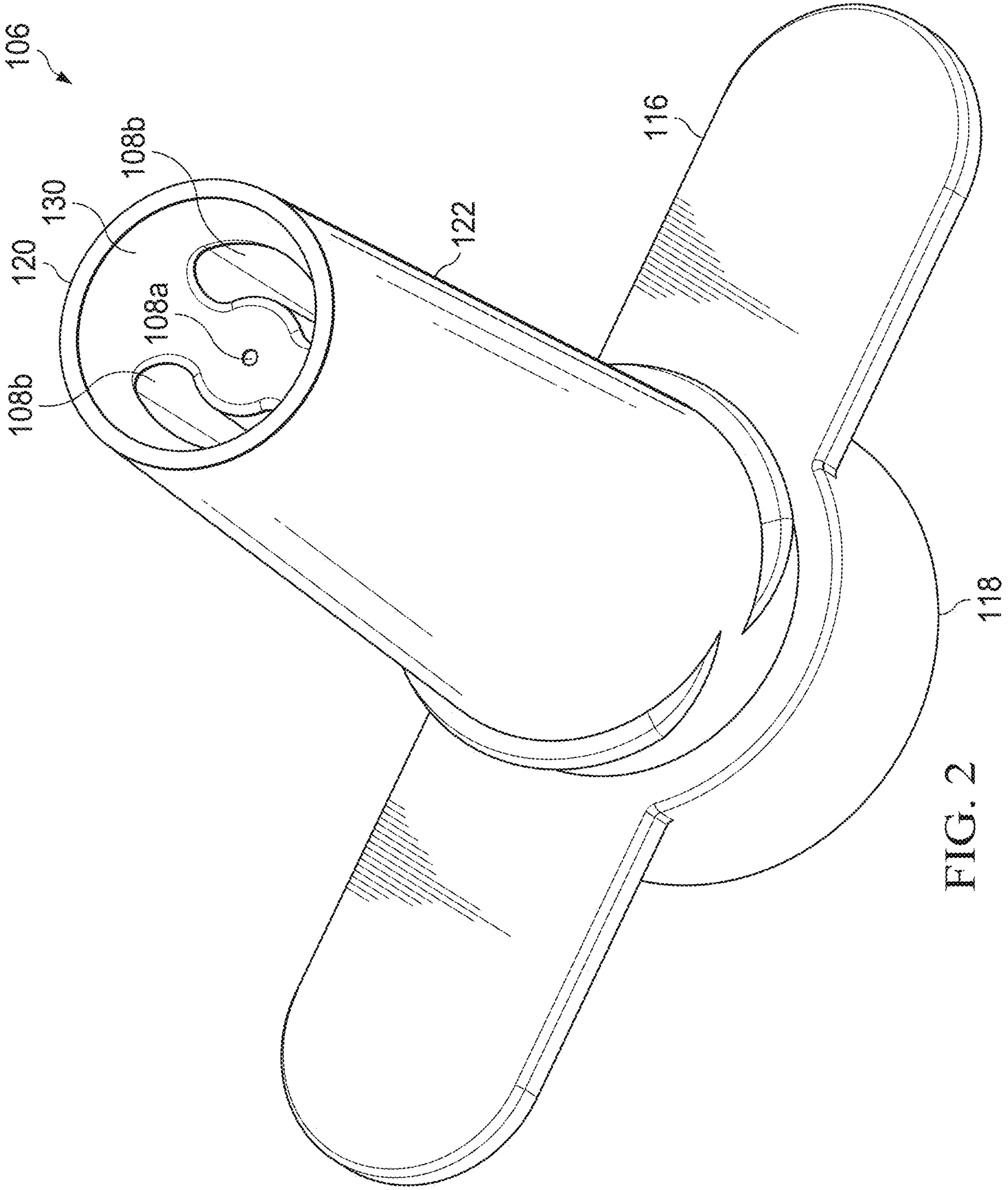
FIG. 2 illustrates a perspective view of a nozzle.

FIG. 2 illustrates a perspective drawing of an embodiment of the nozzle 106. The guard 116 functions as described above and allows for handling and activation of the nasopharyngeal aspirate collection device 100. Orifice 108 is illustrated as three distinct orifices 108*a*, 108*b*. Two orifices are crescent-shaped and are noted by reference marker 108*b*. A central orifice, orifice 108*a*, is disposed in between orifices 108*b* and is generally aligned with the center axis 124 illustrated in FIG. 1B. Fluid from reservoir 102 may be ejected through orifice 108*a* upon actuation of the nasopharyngeal aspirate collection device 100. Withdrawal of the fluid and the specimen to be collected occurs through orifices 108*b* and orifice 108*a* which work in tandem as returns for the specimen when pressure is released from the reservoir 102. The increased size of the orifices 108*b* may help withdrawal larger specimen volumes quickly. The distal end 120 of the nozzle 106 comprises a concave half-dome shaped profile 130. The concave half-dome shaped profile 130 matches a corresponding convex half-dome shaped profile for a cap interior, discussed below.

Figure 3:
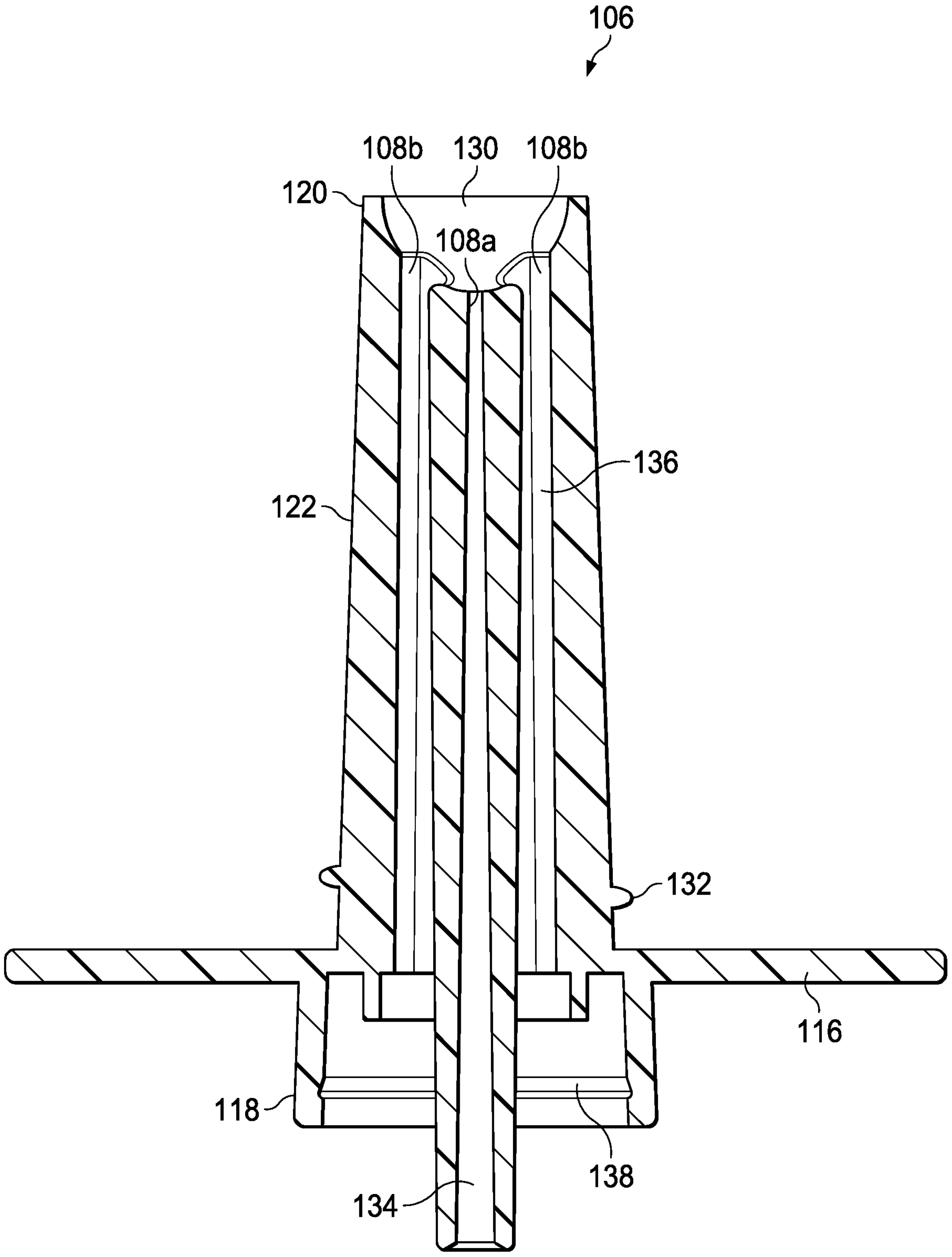
FIG. 3 illustrates a cross-section view of a nozzle.

FIG. 3 illustrates a cross-section of the nozzle 106. As illustrated, the concave half-dome shaped profile 130 descends into the distal end 120 of the nozzle 106. Orifice 108*a* is connected to a central channel 134 which connects to the reservoir 102. Crescent-shaped orifices 108*b* connect to channels 136 which are fluidically coupled to and drain into reservoir 102, but do not descend directly into reservoir 102 in the same manner as channel 134. On the outer surface 122, exterior threads 132 are provided which allow for securing the nozzle 106 to a cap, discussed below. Other fastening means may be used in alternative embodiments.

A diaphragm 138 is disposed within or proximate the interior of the nozzle 106 to control the orifices from which the aspiration fluid may be ejected from. In some examples, the diaphragm may be a part of the reservoir 102. The diaphragm 138 is disposed around the central channel 134 without impediment to the central channel 134. The diaphragm 138 impedes fluid flow in the ejection direction from the reservoir 102 through the channels 136 which lead to orifices 108*b*. As such, the aspiration fluid is only ejected from the reservoir through channel 134 and orifice 108*a*. The diaphragm 138 is a flexible material (e.g., a silicon-based material) which flexes to allow the aspirated fluid to be returned to the reservoir 102 once applied pressure on the reservoir 102 is released and a negative pressure created in the reservoir 102. The aspirated fluid may be returned through orifices 108*a* and 108*b* as the flexibility of the diaphragm 138 is sufficient to allow the aspirated fluid to return to the reservoir 102 in the return direction when negative pressure is applied.

The nasopharyngeal aspirate collection device 100 describe herein may be used to collect a biological sample from the nasal cavity of a subject. The collected biological sample may then be tested on-site using a testing apparatus or the sample may be sent to a lab off-site for further testing. The sample may be tested using any suitable means and should not be limited herein. In certain embodiments, the contaminant load present in the sample may be tested for viruses, microbial infections, bacterial infections, mold, yeast, fungi, cancer cells, substance abuse, external contaminants such as soil, pollutants, toxins, the like, and/or any combinations thereof. The nasopharyngeal aspirate collection device 100 may be a disposable single use device for use at home or in clinic testing. As used herein, it should be understood that "biological sample" and "sample" may be used interchangeably. A biological sample may be sourced from the subject. The subject may include mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

To collect the sample, the user may first obtain the nasopharyngeal aspirate collection device 100 and securely hold the device with one or both of the users hands. In a non-limiting example, two of the users digits may be gripped onto the guard 116 and a third digit may be resting on the outer wall 126 of the enclosed distal end 112 of the reservoir 102. Optionally, the patient may then tilt their head back slightly. The user may then insert at least a portion of the distal end 120 of the nozzle 106 into a nasal cavity of the subject. The nozzle 106 may be positioned in the nasal cavity such that a seal may be formed between the inner wall of the nasal cavity and the outer wall 126 of the nozzle 106. The seal may be formed in any suitable manner and should not be limited herein. In an embodiment, excess air may be released from the nasopharyngeal aspirate collection device 100 before the seal may be formed.

The user may then manually apply force to the outer wall 126 of the distal end of the reservoir 102 such that the reservoir 102 contracts and the aspirate fluid is forced from the reservoir 102, through the nozzle 106, out of the at least one orifice 108 and into the nasal cavity of the user. In certain embodiments, the reservoir 102 may go from a positive pressure environment to a negative pressure environment as the reservoir 102 contracts. The aspirate fluid may then wash the nasal cavity, the nasopharynx, the adenoid pad, the like, and/or any combinations thereof, thereby collecting a biological sample and/or contaminants from the nasal cellular membrane. Optionally, the patient may then return their head to an upright position.

Once a predetermined time has passed, the user may then remove the force applied to the outer wall 126 of the reservoir 102. As the force is removed, the negative pressure environment within the reservoir 102 may then force the sample in the nasal cavity to aspirate. In certain embodiments, the aspirated sample may flow into the device 100 through the at least one orifice 108, through the nozzle 106 and back into the reservoir 102. The nasopharyngeal aspirate collection device 100 may then be used to transfer at least a portion of the collected nasopharyngeal fluid sample to a testing apparatus on site so that the nasopharyngeal fluid sample may be tested and analyzed. Optionally, a cap may be placed on the distal end 120 of the nozzle 106 thereby sealing the nasopharyngeal aspirate collection device 100 with the nasopharyngeal fluid sample inside. The nasopharyngeal aspirate collection device 100 may then be transported to an offsite location for testing and analysis. Any suitable testing apparatus may be used to test the nasopharyngeal sample fluid and should not be limited herein. In a non-limiting example, the sample may be treated before undergoing testing.

Figure 4:
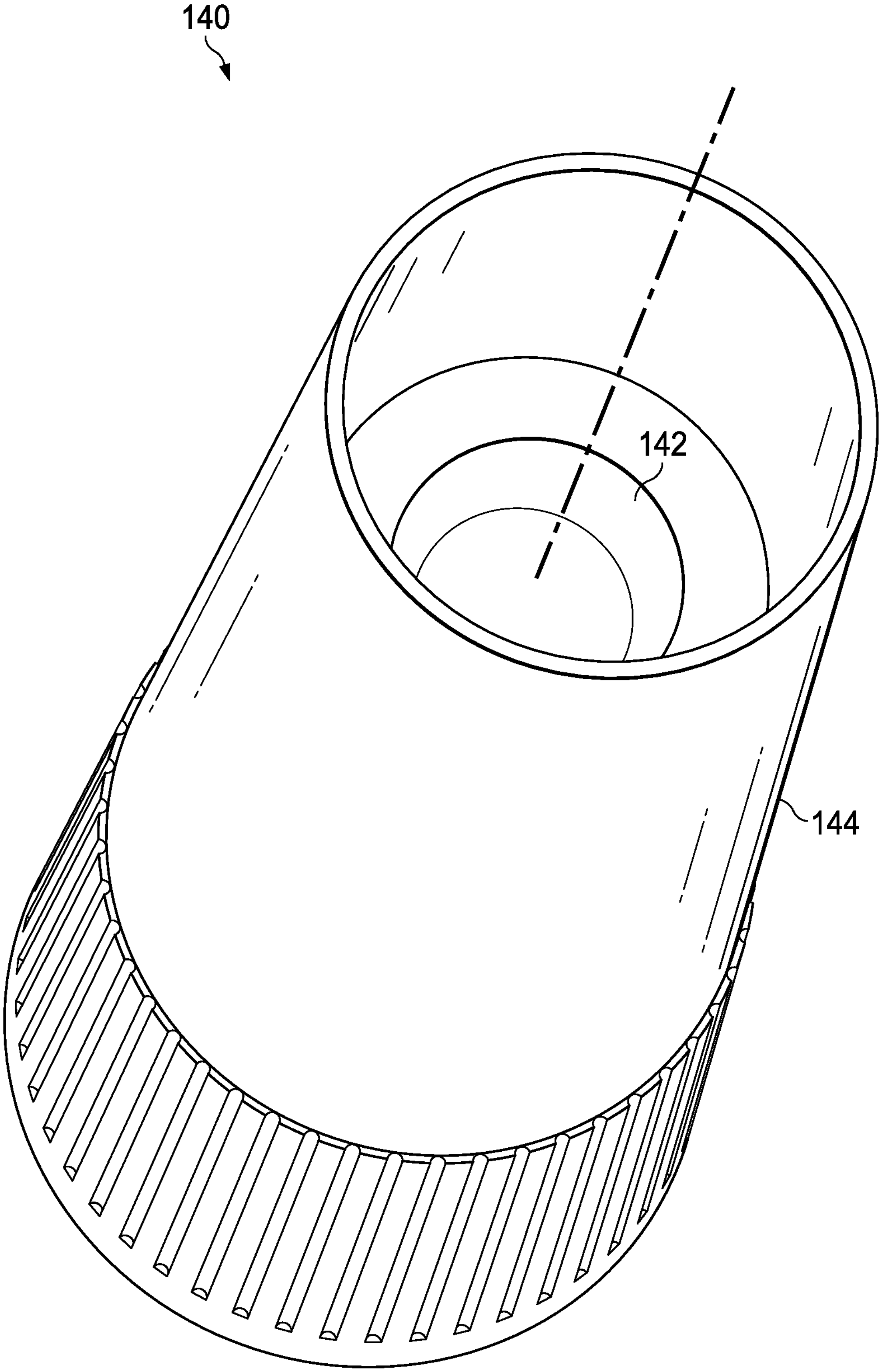
FIG. 4 illustrates a perspective view of a cap.

FIG. 4 illustrates a perspective figure of a cap 140. Cap 140 fits over at least a portion of nozzle 106. Cap 140 contains a convex half-dome shaped profile 142. The convex half-dome shaped profile 142 is convex relative to the corresponding concave half-dome shaped profile 130 of the nozzle 106. The convex half-dome shaped profile 142 fits snugly with the concave half-dome shaped profile 130 of the nozzle 106 when the cap 140 is placed over the nozzle 106. When positioned over the nozzle 106, the cap 140 seals the nozzle 106 through said arrangement to prevent leakage of the collected specimen from the reservoir 102. In some optional embodiments, at least a portion of the outer surface 144 of the cap 140 may be textured to improve gripping and tightening/loosening the cap 140 when placed over the nozzle 106.

Figure 5:
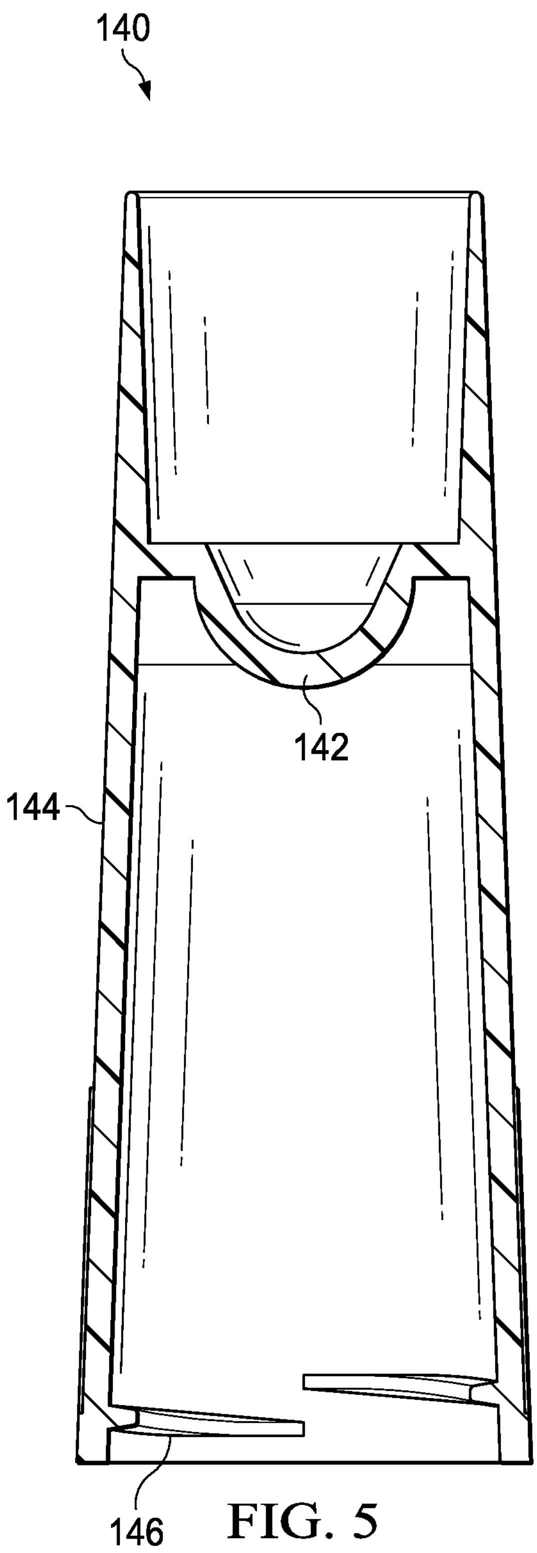
FIG. 5 illustrates a cross-section view of a cap.

FIG. 5 illustrates a cross-section of the cap 140. As illustrated, the convex half-dome shaped profile 142 curves to match the corresponding concave half-dome shaped profile 130 of the nozzle 106 such that the placement of the cap 140 over the nozzle 106 seals the orifices 108 of the nozzle 106. Within the interior of the cap 140, threads 146 may be located for fastening the cap 140 to the nozzle for transport.

In an embodiment, the nasopharyngeal aspirate collection device 100 may be a disposable single use device capable for use at home or in a clinic type atmosphere. In an embodiment, the nasopharyngeal aspirate collection device 100 may be any device capable of providing the washing and aspiration of the aspirate fluid in a single step, which may reduce the time required to collect the sample and may also reduce possible error in collecting the sample.

The figures (Figs.) and the above description may relate to embodiments of the present disclosure by way of illustration only. It may be noted that from the above disclosure, alternative embodiments of the structures and methods disclosed herein may be readily recognized as viable alternatives that may be employed without departing from the principles of what is claimed.

The figures depict embodiments of the disclosed system (or method) for purposes of illustration only. One skilled in the art, along with the present disclosure, may recognize that alternative embodiments of the structures and methods illustrated herein may be employed without departing from the principles described herein.

As used herein any reference to "one embodiment," "an embodiment," or "some embodiments" means that a particular element, feature, structure, or characteristic described in connection with the embodiment may be included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article or apparatus that comprises a list of elements may not necessarily be limited to only those elements but may include other elements not expressly listed or inherent to such process, method, article or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This may be done merely for convenience and to give a

The invention claimed is:

1. A nasopharyngeal aspirate collection device comprising:

a single reservoir capable of contracting and expanding in a lineal motion at least one time;

a nozzle, the nozzle and the reservoir defining an internal cavity extending from an enclosed end of the reservoir through the nozzle and terminating at a first orifice positioned at a tip of the nozzle and at at least one additional orifice positioned at the tip of the nozzle;

a first channel partially defining the internal cavity through the nozzle, the first channel connecting the reservoir to the first orifice, wherein the first channel and the first orifice are centrally positioned in the nozzle;

at least one additional channel partially defining the internal cavity through the nozzle, each of the at least one additional channel connecting the reservoir to a respective one of at least one additional orifice;

a fastening means capable of coupling a proximal end of the reservoir with a proximal end of the nozzle;

a guard disposed about a portion of an outer wall of the reservoir adjacent to the proximal end of the reservoir; and a diaphragm positioned in the nozzle, wherein the diaphragm restricts aspirant fluid from flowing out of the at least one additional channel when pressure is applied to the reservoir, further wherein the diaphragm comprises a flexible material that flexes to allow the aspirated fluid to be returned to the reservoir through the at least one additional orifice once the applied pressure on the reservoir is released and a negative pressure is created in the reservoir, further wherein the diaphragm circumnavigates the first channel as the diaphragm is positioned within the nozzle.

2. The apparatus of claim 1, wherein the nasopharyngeal aspirate collection device is a single use device.

3. The apparatus of claim 1, further comprising a cap.

4. The apparatus of claim 1, wherein the at least one additional orifice comprises two crescent shaped orifices that border the first orifice which is disposed between the two crescent-shaped orifices.

5. The apparatus of claim 1, wherein the distal end of the nozzle comprises a half-domed shape which extends inward toward the proximal end of the nozzle.

6. The apparatus of claim 5, further comprising a cap with a half-domed shape which corresponds to the half-domed shape of the nozzle when the cap is placed over the nozzle.

7. The apparatus of claim 1, wherein the reservoir contains aspiration fluid before use and a collected sample after use.

8. The apparatus of claim 1, wherein the diaphragm comprises silicon.

9. A method for collecting a sample with a nasopharyngeal aspirate collection device, the method comprising:

inserting the nasopharyngeal aspirate collection device into a cavity of a subject, wherein at least a portion of the nasopharyngeal aspirate collection device is prevented from entering the cavity of the subject by a guard disposed on the nasopharyngeal aspirate collection device;

ejecting an aspiration fluid into the cavity from the nasopharyngeal aspirate collection device by applying pressure to a single reservoir containing the aspiration fluid;

using a nozzle to direct the aspiration liquid into the cavity, the nozzle and the reservoir defining an internal cavity extending from an enclosed end of the reservoir through the nozzle and terminating at a first orifice positioned at a tip of the nozzle and at at least one additional orifice positioned at the tip of the nozzle, wherein the aspiration liquid is directed via a first channel partially defining the internal cavity through the nozzle and connecting the reservoir to the first orifice, further wherein the first channel and the first orifice are centrally positioned within the nozzle, further wherein the nasopharyngeal aspirate collection device further comprises a diaphragm which restricts fluid flow outward from the nasopharyngeal aspirate collection device through at least one additional channel, further wherein the diaphragm circumnavigates the first channel as the diaphragm is positioned within the nozzle;

removing pressure from the reservoir to create negative pressure in the reservoir, wherein the diaphragm comprises a flexible material that flexes to allow the aspiration fluid to be returned to the reservoir through the at least one additional channel once the applied pressure on the reservoir is removed and the negative pressure is created in the reservoir; and withdrawing at least a portion of the aspiration fluid and a subject sample from the cavity into the reservoir.

10. The method of claim 9, wherein the method for collecting the sample further comprises:

using a fastening means to couple a proximal end of the reservoir with a proximal end of the nozzle; and the guard is disposed about a portion of an outer wall of the reservoir adjacent to the proximal end of the reservoir.

11. The method of claim 9, further comprising removing the sample from the reservoir by detaching the reservoir; wherein the nasopharyngeal aspirate collection device is disposed of after the sample is removed.

12. The method of claim 9, wherein the method further comprises using the nozzle having the distal end, and wherein the at least one additional orifice comprises two crescent shaped orifices that border the first orifice which is disposed between the two crescent-shaped orifices.

13. The method of claim 12, wherein the method further comprises using the distal end of the nozzle comprises a half-domed shape which extends inward toward the proximal end of the nozzle.

14. The method of claim 13, wherein the method further comprises using a cap with a half-domed shape which corresponds to the half-domed shape of the nozzle when the cap is placed over the nozzle.

15. The method of claim 9, wherein the method further comprises using a reservoir which contains aspiration fluid before use and a collected sample after use.

16. The method of claim 15, wherein the method further comprises using a saline solution for the aspiration fluid.

17. The method of claim 9, wherein the method further comprises inserting the nasopharyngeal aspirate collection device into a nasal cavity.

* * * * *